(12) United States Patent
Lam

(10) Patent No.: US 9,804,162 B2
(45) Date of Patent: Oct. 31, 2017

(54) PLEURAL FLUID MARKERS FOR MALIGNANT PLEURAL EFFUSIONS

(71) Applicant: The University of Hong Kong, Hong Kong (HK)

(72) Inventor: Ching-Wan Lam, Kowloon (HK)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 14/840,909

(22) Filed: Aug. 31, 2015

(65) Prior Publication Data

US 2017/0059571 A1 Mar. 2, 2017

(51) Int. Cl.
| | |
|---|---|
| *G01N 33/00* | (2006.01) |
| *G01N 24/08* | (2006.01) |
| *G01N 33/574* | (2006.01) |
| *G01R 33/465* | (2006.01) |
| *G01N 33/487* | (2006.01) |
| *A61B 5/055* | (2006.01) |

(52) U.S. Cl.
CPC ....... *G01N 33/57423* (2013.01); *G01N 24/08* (2013.01); *G01N 33/487* (2013.01); *G01N 33/57488* (2013.01); *G01R 33/465* (2013.01); *A61B 5/055* (2013.01)

(58) Field of Classification Search
CPC ... G01N 33/57423; G01N 24/08; G01N 33/00
USPC .................................................. 436/43, 131
See application file for complete search history.

(56) References Cited

U.S. PATENT DOCUMENTS

| | | | |
|---|---|---|---|
| 2007/0202515 A1* | 8/2007 | Hadlock et al. | 435/6 |
| 2010/0009858 A1* | 1/2010 | Li | 506/7 |
| 2011/0160290 A1* | 6/2011 | Tewari | 514/44 R |
| 2011/0238319 A1 | 9/2011 | Adamko | |

OTHER PUBLICATIONS

Budczies et al, "Cutoff Finder: a comprehensive and straightforward Web application enabling rapid biomarker cutoff optimization", PLoS ONE, 7 (12):e51862 doi:10.1371 (2012).

Jan, et al., "1H NMR spectroscopic determination of poly 3-hydroxybutyrate extracted from microbial biomass", Enzyme MicrobTechnol, 18:195-201 (1996).

Lam and Law, "Untargeted mass spectrometry-based metabolomic profiling of pleural effusions: fatty acids as novel cancer biomarkers for malignant pleural effusions", J. Proteome Res, 13:4040-6 (2014a).

(Continued)

*Primary Examiner* — Brian J Sines
(74) *Attorney, Agent, or Firm* — Pabst Patent Group LLP (57) ABSTRACT

Methods of diagnosis and/or prognosis of malignant disease from pleural effusion samples are disclosed. The methods typically include determining the normalized intensity of one or more biomarkers, such as acetone and 3-hydroxybutyate, in pleural effusion samples using nuclear magnetic resonance (NMR), such as proton NMR ($^1$H-NMR) spectroscopy. Reference values for malignant disease diagnosis using the disclosed biomarkers are provided. Reference values for prognosis of median survival time based on the disclosed biomarkers are also provided.

17 Claims, 6 Drawing Sheets

(56) References Cited

OTHER PUBLICATIONS

Lam and Law, "Pleural effusion lipoproteins measured by NMR spectroscopy for diagnosis of exudative pleural effusions: a novel tool for pore-size estimation", J. Proteome Res., 13:4104-12 (2014b).

Pontes, et al., "GC determination of acetone, acetaldehyde, ethanol, and methanol in biological matrices and cell culture", J Chromatogr Sci., 47:272-8 (2009).

Porcel and Light, "Diagnostic approach to pleural effusion in adults", Am. Fam. Physician, 73(7):1211-20 (2006).

Tiziani, et al., "Early stage diagnosis of oral cancer using 1H NMR-based metabolomics", Neoplasia, 11:269-76 (2009).

Wang, et al., "Coefficient of Variation, Signal-to-Noise Ratio, and Effects of Normalization in Validation of Biomarkers from NMR-based Metabonomics Studies", Chemometr Intell Lab Syst., 128:9-18 (2013).

Zhou, et al., "Metabonomic classification and detection of small molecule biomarkers of malignant pleural effusions", Anal Bioanal Chem, 404:3123-33 (2012).

\* cited by examiner

PLEURAL FLUID MARKERS FOR MALIGNANT PLEURAL EFFUSIONS

FIELD OF THE INVENTION

The invention is generally directed to the field of disease markers and their rapid detection for prognostic and diagnostic applications.

BACKGROUND OF THE INVENTION

Pleural effusion is an accumulation of fluid between the layers of tissue that line the lungs and chest cavity. Normally, the amounts of pleural fluid are too small to be detectable with routine methods (Zhou et al., *Anal Bioanal Chem*, 404:3123-3133 (2012); Oba et al., *Respiration*, 83(3):198-208 (2012)). In general, a balance between hydrostatic and oncotic pressure is forced in the visceral and parietal pleural vessels and lymphatic drainage (Burgess, *Clin Chim Acta*, 343(1-2):61-84 (2004)). If the balance is disturbed by disorder from all or part of the body, the rate of fluid formation exceeds that of fluid absorption, and unexpected pleural effusion occurs. Excessive amounts of such fluid can impair breathing by limiting the expansion of the lungs during inhalation which predicate the presence of pulmonary, pleural, or extrapulmonary disease (McGrath et al., *Int J Clin Pract*, 63(11):1653-1659 (2009)). In clinic, two different types of effusions can be developed: one is transudative pleural effusion that is caused by fluid leaking into the pleural space; the most common reasons of these effusions are heart failure, cirrhosis, and after surgery. The other is exudative effusion that usually results from leaky blood vessels, and cancer, tuberculosis, pulmonary embolism, and pneumonia account for most exudative effusions.

The first step in the evaluation of pleural effusion is to determine whether the effusion is a transudate or an exudate. For a transudative effusion, therapy should be directed toward the underlying heart failure or cirrhosis. If an effusion is exudative, effort is made to define the etiology.

Based on pathogeny, all of the effusions could be classified as malignant or benign. Malignant pleural effusions (MPEs) usually occur in the setting of cancer, particularly lung and breast cancer are a common clinical problem in patients with primary thoracic and metastatic malignancies to the thorax. The annual incidences of the MPEs are estimated to be about 150,000 to 175,000 cases in the USA and 40,000 in the UK (Uzbeck et al., *Adv Ther*, 27(6):334-347 (2010)). Because the prognosis and strategies of management are very different, differentiation of the MPEs, which might provide the first presenting sign of cancer, from benign pleural effusions (BPEs) is very important in the clinical therapy. Furthermore, even in the same lung cancer patient with pleural effusion, if the right information on the malignancy or benignancy of the effusion is provided, the correct staging and appropriate clinical management could be exerted.

A relatively accurate diagnosis of the cause of the effusion, transudate versus exudate, relies on Light's criteria that is a comparison of the protein and lactate dehydrogenase (LDH) in the pleural fluid to those in the blood; however, about 15 to 25% of patients with transudative pleural effusions are mistakenly identified as exudative ones; thus, additional testing is necessary. The current conventional clinical methods to diagnose MPEs include routine analysis, biochemistry test, and cytological examination. The former two have difficulty in distinguishing MPEs, and the latter is a gold standard to confirm MPEs and has high specificity; however, it is limited by low sensitivity (about 50%) (How et al., *Int Med J*, 4(2):30-37 (2005)). If the result of initial pleural effusion cytology is negative, at least two more pleural fluid specimens must be submitted for further examination, while some MPEs could not be diagnosed even with repeated examinations. Recently, it is popular to analyze levels of tumor markers in pleural effusions to diagnose its malignancy, such as carcinoembryonic antigen (CEA), cancer antigen (CA) 125, CA 19-9, and CA 15-3 [14-16]; however, their sensitivities are quite low, 52.8, 16.7, 52.7, and 50.0% for CEA, CA 125, CA 19-9, and CA 15-3, respectively [13], and their accuracies are still not satisfying, e.g., 85.3, 75.2, 71.5, and 40.5% for CEA, CA 15-3, CA 19-9, and CA 125, respectively (Shitrit et al., *Oncologist*, 10(7):501-507 (2005)).

Currently, there is no rapid and simple test for accurate diagnosis of MPE, or for informing the patients about their prognosis. There is a need for rapid and accurate diagnosis of malignant or benign pleural effusions with minimally invasive techniques. There is also a need for providing disease prognosis to subjects with malignant pleural effusion diagnosis.

Therefore, it is the object of the present invention to provide a method for rapid and accurate diagnosis of malignant disease, such as malignant pleural effusion.

It is a further object of the present invention to provide an accurate prognostic method to predict median survival time of subjects diagnosed with malignant disease, such as malignant pleural effusion.

It is a further object of the present invention to provide kits for the rapid and accurate diagnostic method for diagnosing malignant disease, such as malignant pleural effusion.

SUMMARY OF THE INVENTION

Malignant disease is diagnosed by sampling tissue or fluid from a subject in need of diagnosis, measuring the normalized level, such as the normalized intensity, of a biomarker in the sample, and comparing the normalized level of the biomarker in the sample of the subject in need of diagnosis and the control subject. The subject is diagnosed with malignant disease when the normalized level, such as the normalized intensity, of the biomarker in the sample of the subject in need of diagnosis is at least 1.5 fold greater than the normalized level of the biomarker in the effusion of the control subject.

Typically, the sample is a tissue or fluid sample, such as blood or effusion. In preferred embodiments, the sample is an effusion, including, but not limited to, pleural effusion, pericardial effusion, peritoneal effusion, subdural effusion, or knee effusion. Typically, biomarkers are metabolites of cells, preferably of malignant cells. The biomarkers described herein include, but are not limited to, acetone and 3-hydroxybutyrate.

Typically, prognosis is expressed as months of survival post-diagnosis. In some embodiments, the median survival may be less than six months when the biomarker is acetone at a normalized intensity greater than about 0.25%. The median survival may range from about six months to about 30 months when the normalized intensity of acetone is less than about 0.25%. In other embodiments, the median survival may be less than six months when the biomarker is 3-hydroxybutyrate at a normalized intensity greater than about 0.38%. Also, the median survival may range from about six months to about 30 months when the normalized intensity of 3-hydroxybutyrate is less than about 0.38%.

The normalized level, such as the normalized intensity, of biomarkers can be measured with any suitable instrument used in detecting and analyzing markers in subject's tissue or fluid samples. In some embodiments, the instrument is a spectrometer, such as infrared spectrometer, mass spectrometer, or nuclear magnetic resonance (NMR) spectrometer. In preferred embodiments, the instrument is NMR spectrometer, measuring proton ($^1$H) resonance.

Kits for sampling the tissue or fluid from a subject and detecting one or more biomarkers in the sample may contain buffers for preparing/stabilizing the sample for detection of biomarkers, preparing instruments and software for detection and analysis of biomarkers. The kits may also contain instructions for use, and charts listing normalized intensity of the one or more biomarkers and their associated sensitivity and the specificity for diagnosing and/or prognosis of a malignant disease.

Malignant disease is diagnosed by sampling tissue or fluid from a subject in need of diagnosis, measuring the level of a biomarker in the sample, and comparing the level of the biomarker in the sample of the subject in need of diagnosis and the control subject. The subject is diagnosed with malignant disease when the level of the biomarker in the sample of the subject in need of diagnosis is at least 1.5 fold greater than the normalized level of the biomarker in the effusion of the control subject.

BRIEF DESCRIPTION OF THE DRAWINGS

FIGS. 1A, 1B, and 1C are graphs showing the PE acetone using the 1H NMR spectra from MPE and tuberculous PE (non-MPE) using box plot. The mean acetone level for MPE was 0.25% (95% CI: 0.18-0.31) and the mean acetone level for non-MPE was 0.12% (95% CI: 0.11-0.13) (FIG. 1A). CA stands for carcinoma and represents the MPE. TB stands for tuberculosis and represents non-MPE. Using Student's t-test, the two groups were significantly different with a p-value of 0.0006 and a fold difference of 2.1×. Using acetone for the diagnosis of MPE, the area-under-ROC was determined to be 0.75 (95% CI: 0.59-0.87) with a sensitivity of 64% (95% CI: 42.5-82.0) and a specificity of 93.8% (95% CI: 69.8-99.8) at the optimal cutoff 0.16% with a p-value of 0.0014 (FIGS. 1B and 1C). CA stands for carcinoma and represents the MPE. TB stands for tuberculosis and represents non-MPE.

FIG. 2 is a graph showing PE 3-hydroxybutyrate using the 1H NMR spectra from MPE and tuberculous PE (non-MPE) using box plot. The mean 3-hydroxubytyrate level for MPE was 0.46% (95% CI: 0.32-0.61) and the mean 3-hydroxubytyrate level for non-MPE was 0.26% (95% CI: 0.23-0.29). Using Student's t-test, the two groups were significantly different with a p-value of 0.0091 and a fold difference of 1.8×. Using 3-hydroxubytyrate for the diagnosis of MPE, the area-under-ROC was determined to be 0.68 (95% CI: 0.51-0.81) with a sensitivity of 64% (52% CI: 31.3-72.2) and a specificity of 93.8% (95% CI: 69.8-99.8) at the optimal cutoff 0.33% with a p-value of 0.04.

DETAILED DESCRIPTION OF THE INVENTION

I. Definitions

As used herein, the term "diagnosing" refers to steps taken to identify the nature of a disease or condition that a subject may be suffering from. As used herein, the term "diagnosis" refers to the determination and/or conclusion that a subject suffers from a particular disease or condition.

As used herein, the term "prognosis" relates to a scientifically-deduced prediction of a disease course, disease duration, and/or expected survival time. A complete prognosis may include the expected duration, the function, and a description of the course of the disease, such as progressive decline, intermittent crisis, or sudden, unpredictable crisis, as well as duration of the disease, or mean/median expected survival. Typically, scientifically-deduced prognosis is based on information gathered from various epidemiologic, pathologic, and/or molecular biologic studies involving subjects suffering from a disease for which a prognosis is sought.

As used herein, the term "normalized level" refers to the percentage of the level of a given marker over the baseline level. The level of a marker can be measured in suitable category, such as amount, amount per unit, concentration, signal intensity, NMR intensity, etc. For example, when the level used is NMR intensity, the normalized level can be the percentage of NMR intensity for the marker over the NMR intensity of the entire sample (also referred to as "total intensity").

As used herein, the term "normalized intensity" refers to the percentage of the intensity of a given marker over the intensity of the entire sample (also referred to as "total intensity"), obtained using proton NMR.

As used herein, the term "total intensity" refers to the proton NMR intensity of the entire test sample, calculated over the range of 0.1 to 10 ppm, and represents the sum of intensities of individual intervals obtained with rectangular bucketing and spanning the range of 0.1 to 10 ppm, minus the intensity of the subregion from 4.45 to 4.90 ppm, representing the subregion for water signals. The rectangular bucketing may represent an interval size ranging, for example, from between 0.01 and 0.05 ppm, which includes values of 0.01 ppm and 0.05 ppm. Examples of interval sizes include 0.01 ppm, 0.015 ppm, 0.02 ppm, 0.025 ppm, 0.03 ppm, 0.035 ppm, 0.04 ppm, 0.045 ppm, 0.05 ppm, 0.055 ppm, 0.06 ppm, 0.065 ppm, 0.07 ppm, 0.08 ppm, 0.085 ppm, 0.09 ppm 0.095 ppm, and 0.10 ppm. A preferred interval size is 0.04 ppm. The interval size is kept constant for measuring the normalized intensities of markers between samples. The subregion, representing the water signals, is typically present from 4.45 to 4.90 ppm and is excluded from the calculation of total intensity to reduce variability from the water signals.

As used herein, the term "proliferative disease" refers to a disease excessive proliferation of cells and turnover of cellular matrix, such as cancer, idiopathic pulmonary fibrosis, scleroderma and cirrhosis of the liver. Proliferative disease may be malignant or benign.

As used herein, the term "malignant disease" refers to a disease that is not self-limiting, so that the disease spreads and invades tissues of a subject other than the tissue the disease originated in. Malignant disease, such as cancer, is often characterized by presence of altered cells in a subject, wherein altered cells are cells with lost morphological characteristics and structural differentiation (anaplastic cells), acquisition of invasiveness by such cells, and metastasis to other tissues within the subject.

As used herein, the term "benign disease" refers to a disease caused by noncancerous, i.e., non-invading, cells, marked by an increase in the growth of the cells.

As used herein, the term "sampling" refers to collecting a sample, such as tissue or fluid sample, from a subject. The sample may be collected by any suitable means, including a device, such as a biopsy needle, a syringe, a catheter, a cannula. The sample may also be provided by the subject, such as a sample of urine, saliva, sputum, tears, blood, etc.

As used herein, "effusion" refers to the seeping of fluid into a body cavity; also to the fluid itself; an abnormal collection of fluid in a body cavity or space, such as around one or both lungs in the pleural cavity (pleural effusion), around the heart in the pericardial cavity (pericardial effusion), in the abdominal cavity (peritoneal effusion), around the brain and between the brain and the outer lining of the brain (subdural effusion), or in or around the knee joint (knee effusion).

As used herein, the term "subject in need of diagnosis" refers to a subject, such as a vertebrate animal, preferably a mammal, in need of determining presence or absence of a proliferative disease in the subject, and/or whether the proliferative disease is malignant or benign.

As used herein, the term "subject in need of prognosis" refers to a subject, such as a mammal, in need of a prediction of subject's disease course, disease duration, and/or expected survival time.

As used herein, the term "control subject" refers to a subject, such as a mammal, without known or suspected case of proliferative disease.

As used herein, the term "measuring," in the context of the disclosed method, refers to one or more steps taken to measure a level, an intensity (such as a normalized intensity), an amount, a volume, etc., for a given substance, molecule, or compound. Measuring may require simple reading of a value from a beaker containing the given substance, molecule, or compound. Alternatively, measuring may require the steps of preparing a sample containing the given substance, molecule, or compound, preparing several samples of standards or controls containing a known amount of the given substance, molecule, or compound, allowing the sample, the standards, and/or the controls to enter and be detected by an instrument, such as a spectroscopy, chromatography, and/or electrophoresis instrument, converting the values presented by the instrument into values for the normalized level, intensity (such as the normalized intensity), the amount, the volume, etc., for the given substance, molecule, or compound, using the values obtained from the standards and/or control samples.

As used herein, the term "biomarker" or "marker" refers to a substance, molecule, or compound that is produced by, synthesized, secreted, or derived, at least in part, from the cells of the subject and is used to determine presence or absence of a disease, and/or the severity of the disease.

As used herein, the term "fold" refers to a difference in the number of times. For example, "1.5 fold greater than" refers to a value that is 1.5 as large as a given reference value. Fold values can also be expressed in percentage. For example, 1.5 fold is equivalent to 150% of the reference value.

As used herein, the term "median survival" refers to the length of time from either the date of diagnosis or the start of treatment for a disease, such as cancer, during which half of the patients in a group of patients diagnosed with the disease are still alive.

As used herein, the term "sensitivity" refers to the proportion of actual positives which are correctly identified as such (e.g. the percentage of sick people who are correctly identified as having the condition).

As used herein, the terms "selectivity" and "specificity" refer to the proportion of negatives which are correctly identified as such (e.g. the percentage of healthy people who are correctly identified as not having the condition).

II. Compositions

A. Biomarkers.

One or more biomarkers for diagnosis and/or prognosis of a malignant disease include, but are not limited to, acetone, 3-hydroxybutyrate, 1-methylhistamine, 1-methylnicotinamide, 2-methylglutarate, 2-oxoglutarate, 3-OH-3-methylglutarate, 3-methyladipate, 4-aminohippurate, acetone, adenine, alanine, creatine, dimethylamine, formate, fumarate, glucose, glycolate, imidazole, lactate, methylamine, O-acetylcarnitine, oxalacetate, phenylacetylglycine, phenylalanine, tryptophan, tyrosine, cis-aconitate, myo-inositol, trans-aconitate, leucine, valine, acetate, acetoacetate, creatinine, and trimethylalanine-N-oxide. In preferred embodiments, the biomarker is acetone, 3-hydroxybutyrate, or a combination thereof.

Typically, the biomarker is detected in sample taken from a subject in need of diagnosis and/or prognosis. Optionally, the biomarker can be detected in a sample taken from a control subject.

B. Samples Containing Biomarkers.

The biomarkers may be measured from any sample obtained from a subject in need of diagnosis or a control subject. The sample may be tissue or fluid from a subject.

1. Tissue Samples.

In some embodiments, the one or more biomarkers are detected and measured in one or more tissue samples from the subject. Suitable tissue samples include, but are not limited to, tumor tissue, or tissue from an organ, such as from lung, muscle, intestine, liver, kidney, spleen, and lymph node.

2. Fluid Samples.

In some embodiments, the one or more biomarkers are detected and measured in one or more fluid samples from the subject. Suitable fluid samples include, but are not limited to, blood, plasma, lymph, pleural fluid, peritoneal fluid, pericardial fluid, synovial fluid, cerebrospinal fluid, aqueous humor, urine, saliva, sputum, and tears.

In preferred embodiments, the fluid is an effusion, including, but not limited to, pleural, peritoneal, pericardial, synovial, knee, and/or subdural effusion. In the most preferred embodiment, the fluid is pleural effusion.

3. Collecting Samples.

The tissue or fluid sample may be collected by any suitable means, including with a device such as a biopsy needle, a syringe, a catheter, a cannula. The sample may also be obtained non-invasively and/or provided by the subject, such as a sample of urine, saliva, sputum, tears, blood, etc.

4. Preparing Samples.

Before a biomarker can be measured from a sample, the sample may be pre-treated by the addition of a stabilizing solution, such as a buffer, or by preparing the sample using centrifugation. For example, the samples can be centrifuged to obtain a clear supernatant for testing. Typically, the centrifugation is carried out at 3000 rpm for 10 min, at 4° C.

III. Kits

Kits containing devices for sampling tissue or fluid of a subject in need of diagnosis and/or prognosis, and one or more containers with buffers for preparing tissue or fluid samples for detection of one or more biomarkers are also provided herein. The kits can also include an instruction manual for sampling the tissue or fluid from a subject and for preparing the sample for detection of the one or more biomarkers. Kits may also include instructions on instrument and/or software settings for detecting the biomarkers and obtaining normalized level, such as the normalized intensity, of the biomarkers in the sample using a given method of detection.

Optionally, the kits can include charts listing normalized intensity of the one or more biomarkers and their associated sensitivity and the specificity for diagnosing a malignant disease. The kits can also include charts listing normalized intensity of the one or more biomarkers and their associated prognosis for a given malignant disease.

IV. Methods of Detection

Methods of detection of biomarkers in vitro include, but are not limited to, chromatography, spectroscopy, and enzymatic or colorimetric detection.

Examples of spectroscopic methods include NMR spectroscopy (as detailed in Zhou et al., *Anal Bioanal Chem*, 404:3123-3133 (2012); Jan et al., *Enzyme MicrobTechnol*, 18:195-201 (1996); and in U.S. patent application publication No. US 2011/0238319), IR spectroscopy and mass spectroscopy. Other methods of detection include gas chromatography with flame ionization detection. Any suitable method able to measure the normalized intensity of the biomarkers in tissue or fluid samples can be used. In preferred embodiments, the detection method is $^1$H NMR spectroscopy.

A. NMR Spectroscopy.

An exemplary method of preparing a sample for NMR is provided in the Example below. Samples can be collected or transferred into sterile containers. The samples can be centrifuged to obtain a clear supernatant for testing. An exemplary centrifugation step is 3000 rpm for 10 minutes at 4° C. The sample can be stored frozen, for example at −20° C., −80° C., or −120° C. At the time of analysis, the sample can be mixed with a buffer suitable for NMR analysis.

An exemplary buffer is a solution of 100 mM phosphate buffer in 100% $D_2O$ containing 0.1% trimethylsilyl propionic acid (TSP) in a 1:2 ratio (v/v).

An exemplary mixing of sample and buffer is a ratio of 4 parts sample to 1 part buffer (i.e., 480 µL of sample and 120 µL of buffer solution). NMR can be carried out with small volume samples. An exemplary NMR sample is about 550 µL including both sample and buffer. NMR provides a number of advantages over alternative methods of measuring biomarkers. As discussed above, samples suitable for NMR can be prepared by mixing the sample directly with buffer, and typically do not require any chemical reactions. NMR instrumentation can be equipped with an automated sample delivery system in which multiple samples can be analyzed in parallel.

In some embodiments, however, one of more other in vitro techniques for measuring biomarkers is used in addition to, or as an alternative to, NMR. Other techniques for quantifying or profiling biomarkers in biological sample are known in the art. The methods include infrared spectroscopy, mass spectroscopy (as detailed in Lam et al., *J. Proteome Res*, 13:4040-4046 (2014), and chromatography, such as gas chromatography with flame ionization detection, as detailed in Pontes et al., *Journal of Chromatographic Science*, 47:272-278 (2009)).

1. Instrument Adjustment for Detecting Biomarkers.

Standard instrument settings for detecting analytes in biological samples can be used. An exemplary instrument with settings adjusted to detect biological analytes is presented below, but other instruments with suitable adjustments to detect biological analytes may also be used.

For example, high-resolution proton NMR detection can be performed using a Bruker Avance 600 MHz NMR spectrometer (Bruker Biospin, Rheinstetten, Germany) equipped with a 5 mm PABBI proton probe. Chemical shifts of the spectra can be referenced to an internal standard, such as trimethylsilyl propionate (TSP). Spectra can be recorded with a spectral width of 12019.230 Hz, at 298 K, into 32K data points before Fourier transformation. The spectra from the analytes can be recorded using suitable software, such as the ICON-NMR software (Bruker BioSpin). A Carr-Purcell-Meiboom-Gill (CPMG) pulse program may be applied for acquisition of all $^1$H NMR spectra with water presaturation using a "cpmgpr1d" (Bruker pulse program). All spectra may be reduced to data using Amix (version 3.9.11, Bruker BioSpin) using rectangular bucketing at an interval of 0.01 ppm over the range of 0.1 to 10.0 ppm. The processed data may be normalized using the total intensity.

2. Quantifying Biomarkers.

The level of one or more biomarkers can be measured using any suitable techniques. The measured level can be, for example, amount, amount per unit, concentration, signal intensity, NMR intensity, etc. Levels can be measured or expressed as relative values or absolute values.

a. Relative Quantitation.

Biomarker concentrations (such as acetone and 3-hydoxybutyrate) can also be presented qualitatively as ratios (e.g., relative to a standard such as another metabolite in the sample, or the same metabolite in a control sample) rather than as absolute concentrations (also referred to as relative quantification). One of the simplest approaches is the internal endogenous marker method. With this approach, one of the measured peaks, originating from an endogenous metabolite, serves as a concentration standard. Peak ratios (possibly corrected for factors such as relaxation) are converted into concentrations by using a value for the reference metabolite, whose concentration is invariant in the sample.

Data analysis for absolute and relative data quantitation can include a number of techniques which are known in the art and include, for example, integration and peak fitting. See, for example, Jansen, et al., *Radiology*, 240:318-332 (2006), which provides methods and techniques for system calibration and data analysis that can be used for absolute and relative quantification of NMR data in vitro and in vivo.

b. Absolute Quantitation.

As discussed in Cheung, et al., *Acad. Radiol.*, 18:377-383 (2011), Petersen, et al., *Clinical Chemistry*, 51(8):1457-1461 (2005), Otvos, et al., *Clinical Chemistry*, 38(9):1632-1638 (1992), and Otvos, et al., *Clinical Chemistry*, 37(3):377-386 (1991), NMR can be used to profile and quantitate absolute values of biomarkers. The absolute values determined using NMR are generally found to correlate well with the values measured using other methods of measurement including ultracentrifugation. Therefore, in some embodiments, the level of biomarkers in pleural fluid is measured as an estimated or precise absolute quantitative value corresponding to the actual level of the biomarker fluid sample.

Absolute quantification (AQ), also referred to as absolute quantitation) implies that concentrations are expressed in biochemical units. The corresponding metabolites in the pleural fluid sample have certain resonance frequencies, line widths (full width at half maximum of the peak's height), line shapes (e.g., lorentzian or Gaussian), phases, and areas. The peaks are separated owing to differences in resonance frequency, which are caused by the difference in the chemical environment of the different nuclei. The molecular structure of metabolite is reflected by its characteristic peak pattern. The area of a peak is directly proportional to the number of nuclei that contribute to it and to the concentration of the metabolite to which the nuclei belong. However, the peak areas are also influenced by other factors, including T1 and T2 relaxation times.

Generally, for absolute quantification, accurate peak areas for the relevant metabolites are determined and careful calibration is used to convert peak areas to metabolite concentrations to which the metabolite signals are referenced.

c. Normalized Level.

The biomarker may be represented by its normalized level, such as its normalized intensity, in a sample, rather than its concentration. The normalized level is generally referred to the percentage of the level of a given marker over the baseline level of the sample or a control sample. The normalized intensity is generally referred to by the percentage of the intensity of a given marker over the total intensity of the sample obtained using proton NMR.

Typically, the normalized level, such as the normalized intensity, of a biomarker in a test sample or in a control sample is measured using the same instrument settings and data analysis parameters. Examples of measuring normalized intensities of metabolites using proton NMR are presented in Lam et al., *J. Proteome Res.*, 13:4104-4112 (2014). The parameters measuring the normalized intensity, such as bucket interval size, and the range used to calculate total intensity, are kept constant during analysis. The total intensity for the entire test sample is calculated over the range of 0.1 to 10 ppm, and represents the sum of intensities of individual intervals obtained with rectangular bucketing and spanning the range of 0.1 to 10 ppm, minus the intensity of the subregion from 4.45 to 4.90 ppm, representing the subregion for water signals. The rectangular bucketing may represent an interval size ranging, for example, from between 0.01 and 0.05 ppm, which includes values of 0.01 ppm and 0.05 ppm. Examples of interval sizes include 0.01 ppm, 0.015 ppm, 0.02 ppm, 0.025 ppm, 0.03 ppm, 0.035 ppm, 0.04 ppm, 0.045 ppm, 0.05 ppm, 0.055 ppm, 0.06 ppm, 0.065 ppm, 0.07 ppm, 0.08 ppm, 0.085 ppm, 0.09 ppm 0.095 ppm, and 0.10 ppm. A preferred interval size is 0.04 ppm. In preferred embodiments, the interval size for rectangular bucketing is 0.04 ppm or 0.01 ppm.

The normalized intensities for biomarkers may range from between 0.05% and 1%. In preferred embodiments, the normalized intensities of biomarkers range from 0.1 to 0.8%.

As an example, the normalized intensity of both acetone (intensity at 2.22 ppm divided by the total intensity after excluding the region 4.45-4.90 ppm) and 3-hydroxybutyrate (intensity at 1.18 ppm divided by the total intensity after excluding the region 4.45-4.90 ppm) can be measured.

3. Comparison to a Control.

Once the data is quantified, it is compared to a control or standard to determine if the biomarker has an increased level (such as increased concentration or normalized intensity) relative to the control or a standard value. The control can be an absolute value or range of absolute values. The control can be a relative value or range of relative values.

One of skill in the art will understand how to prepare or select an appropriate control based on the nature of the test sample. The values or range of values for controls can be determined using any suitable method known in the art, including those discussed herein such as NMR. In a preferred embodiment, the values for the control samples are determined in the same manner or using the techniques and protocols as is used to determine the value(s) of the test sample. Control values are typically obtained from normal individuals, preferably multiple individuals to provide a statistically significant normal range. In some embodiments, the control values are obtained from individuals, preferably multiple individuals, who have a diagnosis of a disease other than a proliferative disease.

V. Methods of Use

The biomarkers can be used to diagnosis the presence or absence of a malignant disease or for prognostic purposes, such as for predicting a malignant disease outcome. Typically, elevated normalized level, such as elevated normalized intensity, of one or more biomarkers in subject's sample relative to those in a sample from a control subject, or relative to a reference value, indicate presence of a malignant disease and support the diagnosis of malignant disease.

A. Methods of Diagnosis.

The methods of diagnosis of malignant disease disclosed herein can be used alone or in combination with other diagnostic methods, including, but not limited to, cytology, histopathology, non-invasive imaging, and/or clinical assessment, to diagnose a subject with a malignant proliferative disease, such as malignant pleural effusion. Diagnosis can be made using any suitable level or value of the biomarkers. Examples below (involving normalized intensity and concentration) can be analogized to other levels and values. Diagnosis using biomarker normalized intensity is preferred.

1. Diagnosis Using Biomarker Normalized Intensity.

The method of diagnosis includes measuring the normalized intensity of biomarkers in samples obtained from a subject in need of diagnosis (test sample), and comparing the values to those from a control subject (control sample). The normalized intensity of biomarkers in the test sample and control sample is then compared to determine if the test sample includes at least 1.5 fold greater normalized intensity of a given biomarker. The fold difference between the test sample and the control sample can be as little as 1.5 fold or as high as fifty fold, or greater normalized intensity of the biomarker in the test sample when compared to that of the control sample. In some embodiments, this fold difference indicates that the test sample has a malignant disease origin.

Alternatively, the method of diagnosis may include comparing the normalized intensity of the biomarker in the test sample to a reference value. For example, the reference value for a given biomarker can be provided as a chart, and a fold increase in the range of about 1.5 fold to fifty fold over the reference normalized intensity for the given biomarker may indicate presence of a malignant proliferative disease, such as a malignant pleural effusion.

Therefore, diagnosing the subject in need of diagnosis with malignant disease can be made when the normalized intensity of the biomarker in the effusion of the subject is at least 1.5 fold greater than the normalized intensity of the biomarker in the effusion of the control subject, or the reference normalized intensity.

2. Diagnosis Using Biomarker Concentration.

The method of diagnosis includes measuring the concentration of biomarkers in samples obtained from a subject in need of diagnosis (test sample), and comparing the values to those from a control subject (control sample). The concentration of biomarkers in the test sample and control sample is then compared to determine if the test sample includes at least two fold greater concentration of a given biomarker. The fold difference between the test sample and the control sample can be as little as two fold or as high as fifty fold, or greater concentration of the biomarker in the test sample when compared to that of the control sample. In some embodiments, this fold difference indicates that the test sample has a malignant disease origin.

Alternatively, the method of diagnosis may include comparing the concentration of the biomarker in the test sample to a reference value. For example, the reference value for a given biomarker can be provided as a chart, and a fold increase in the range of about two fold to fifty fold over the reference concentration for the given biomarker may indicate presence of a malignant proliferative disease, such as a malignant pleural effusion.

In some embodiments, the reference concentration for acetone is about 0.03 mmol/L, and for 3-hydroxybutyrae is about 0.13 mmol/L. In some embodiments, diagnosis of malignant disease is made when the concentration of acetone in the test sample ranges from between 0.03 mmol/L and 1 mmol/L. Additionally or alternatively, diagnosis of malignant disease is made when the concentration of 3-hydroxybutyrate in the test sample ranges from between 0.13 mmol/L and 2 mmol/L.

As an example, diagnosis can be made using the normalized intensity of both acetone (intensity at 2.22 ppm divided by the total intensity after excluding the region 4.45-4.90 ppm) and 3-hydroxybutyrate (intensity at 1.18 ppm divided by the total intensity after excluding the region 4.45-4.90 ppm).

3. Other Diagnostic Procedures

In some embodiments, the methods of diagnosis disclosed herein are combined with additional diagnostic procedures, such as those discussed in Porcel, et al., *Am. Fam. Physician*, 1; 73(7):1211-1220 (2006). For example, Helical CT can be used to diagnose deep venous thrombosis when combined with CT venography of the pelvis and lower extremities, and can distinguish malignant from benign pleural disease. CT findings indicative of malignant disease are the presence of pleural nodules or nodular pleural thickening, circumferential or mediastinal pleural thickening, or infiltration of the chest wall or diaphragm. Positron emission tomography (PET) has also been used to distinguish between benign and malignant pleural diseases. Additional diagnostic methods are in addition to the classification of the pleural fluid.

Bronchoscopy is useful whenever an endobronchial malignancy is likely, as suggested by one or more of the following characteristics: a pulmonary infiltrate or a mass on the chest radiograph or CT scan, hemoptysis, a massive pleural effusion, or shift of the mediastinum toward the side of the effusion.

Closed-needle biopsy of the pleura for histologic examination classically has been recommended for undiagnosed exudative effusions when tuberculosis or malignancy is suspected. The combination of histology (80 percent sensitivity) and culture (56 percent sensitivity) of pleural biopsy tissue establishes the diagnosis of tuberculosis in up to 90 percent of patients. This diagnosis is also strongly suggested by a high ADA level in the pleural fluid as discussed above.

Cytology is superior to blind pleural biopsy for the diagnosis of pleural malignancy. The diagnostic yield from pleural biopsy is typically higher when it is used with some form of image guidance to identify areas of particular thickening or nodularity.

Thoracoscopy is diagnostic in more than 90 percent of patients with pleural malignancy and negative cytology. Therefore, it is a preferred diagnostic procedure in patients with cytology-negative pleural effusion who are suspected of having pleural malignancy. Thoracoscopy also offers the possibility of effective pleurodesis during the procedure.

B. Methods of Prognosis.

Provided herein are also methods of determining disease prognosis for a subject with a malignant disease. The method includes sampling a test sample from the subject in need of prognosis, measuring the normalized level, such as the normalized intensity or the concentration, of a biomarker in the sample, and comparing the value with levels correlated with median survival time. Typically, the median survival time of less than about six months indicates a short disease course, and a median survival time of more than about six months indicates a long disease course.

For prognostic applications, measuring the normalized level, such as the normalized intensity or the concentration, of the biomarker can be carried out as described above. A cutoff level for each of the biomarkers can be determined using methods known in the art (Budczies et al., *PLoS ONE*, 7(12):e51862. doi:10.1371/journal.pone.0051862(2012)) and establish long or short term for the disease course. In embodiments in which the biomarker is acetone, short disease course can be expected when the normalized intensity of acetone in a sample collected from a subject in need of prognosis is greater than about 0.25%. If the concentration of acetone in the sample is used for prognostic purposes, then short disease course can be expected when acetone concentration in a sample collected from a subject in need of prognosis is greater than about 0.11 mmol/L, and ranges from between 0.11 mmol/L and 1 mmol/L. Conversely, a long disease course can be expected when the normalized intensity of acetone in a sample collected from a subject in need of prognosis is less than about 0.25%. If the concentration of acetone in the sample is used for prognostic purposes, then long disease course can be expected when acetone concentration in a sample collected from a subject in need of prognosis is less than about 0.11 mmol/L, and ranges from between 0.03 mmol/L and 0.11 mmol/L.

In another embodiment in which the biomarker is 3-hydroxybutyrate, short disease course can be expected when the normalized intensity of 3-hydroxybutyrate is greater than about 0.38%. If the concentration of 3-hydroxybutyrate in the sample is used for prognostic purposes, then short disease course can be expected when the concentration of 3-hydroxybutyrate is greater than about 0.44 mmol/L, and ranges from between 0.44 mmol/L and 2 mmol/L. Conversely, a long disease course can be expected when the normalized intensity of 3-hydroxybutyrate in a sample collected from a subject in need of prognosis is less than about 0.38%. If the concentration of 3-hydroxybutyrate in the sample is used for prognostic purposes, then long disease course can be expected when the concentration of 3-hydroxybutyrate is less than about 0.44 mmol/L, and ranges from between 0.13 mmol/L and 0.44 mmol/L.

The present invention will be further understood by reference to the following non-limiting examples.

EXAMPLES

Example 1. NMR-Based Metabolomics Detect Diagnostic Biomarkers for MPE

PE metabolomes were studied using both NMR based metabolomic profiling and orthogonal partial least squares (OPLS) regression analysis.

Materials and Methods

Patients' samples were analyzed for a full spectrum of biological analytes.

Patients

Patients with MPE were followed up for 4 years. In this study, 41 pleural effusions from 25 patients with malignant pleural effusions, 16 patients with pulmonary tuberculosis (TB) were recruited.

Diagnostic Criteria

The diagnosis of malignant pleural effusions was based on (i) the cytology of the pleural fluid, (ii) the histopathology of the pleural biopsy, and/or (iii) clinical assessment. For benign pleural effusion, samples with the diagnosis of pulmonary tuberculosis (TB, another common cause) were selected as controls. The diagnosis was based on the presence of granulomatous inflammation with a positive Ziehl-Neelsen (ZN) stain. The following microbiological evidence was considered if the ZN stain was negative: (i) *Mycobacterium tuberculosis* organisms cultured from pleural fluid and/or pleural biopsy specimen, (ii) positive sputum culture for TB, and/or (iii) positive identification of TB using polymerase chain reaction (PCR) from the pleural fluid samples.

NMR Analysis

All of the high-resolution proton NMR experiments were performed using a Bruker Avance 600 MHz NMR spectrometer (Bruker Biospin, Rheinstetten, Germany) equipped with a 5 mm PABBI proton probe. Chemical shifts of the spectra were referenced to the internal standard of trimethylsilyl propionate (TSP). Spectra were recorded with a spectral width of 12019.230 Hz, at 298 K, into 32K data points before Fourier transformation. All spectra were recorded using an automatic sample changer, SampleXpress (Bruker Biospin), and the ICON-NMR software (Bruker BioSpin). Automatic tuning, frequency-locking on D2O, and shimming were performed using ICON-NMR before data acquisition. A Carr-Purcell-Meiboom-Gill (CPMG) pulse program was applied for acquisition of all $^1$H NMR spectra with water presaturation using a "cpmgpr1d" (Bruker pulse program). The spectral parameters used were four dummy acquisitions, followed by 64 acquisitions. Phase and baseline were corrected automatically with manual adjustment if needed and referenced to the internal standard TSP (0.000 ppm) using TopSpin (version 3.1, Bruker BioSpin, Rheinstetten, Germany). All spectra were reduced to data using Amix (version 3.9.11, Bruker BioSpin) using rectangular bucketing at an interval of 0.01 ppm over the range of 0.1 to 10.0 ppm. The subregion 4.45 to 4.90 ppm was removed to reduce the variability introduced from water signals. The processed data were normalized using the total intensity.

Results

After a 4 years follow up, the patients were divided into long and short survival subgroups. The metabolites acetone and 3-hydroxybutyrate were identified as the two major diagnostic biomarkers, because these were at significantly greater levels in the MPE patients when compared to those of the non-MPE controls. The high PE acetone and 3-hydroxybutyrate were associated with a more invasive cancer and a poor survival outcome. Because PE is the natural reservoir of cancer and cancer-stromal metabolites, the activity of cancer-stromal metabolic coupling can be determined by measuring the normalized intensity of acetone and 3-hydroxybutyrate in MPE.

Using orthogonal partial least squares (OPLS) regression analysis, acetone and 3-hydroxybutyrate signals were found to be specifically elevated in MPE with poor survival.

Figure 1A:
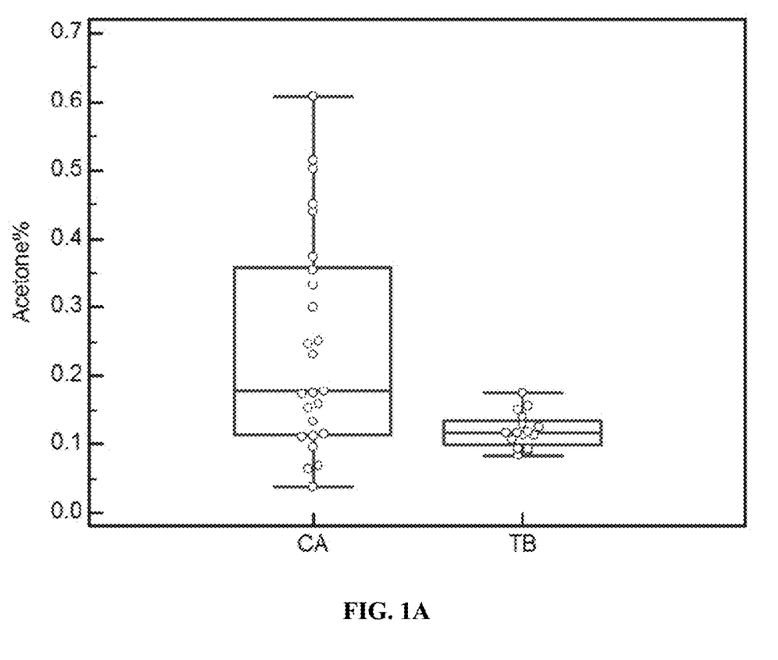
Figure 1B:
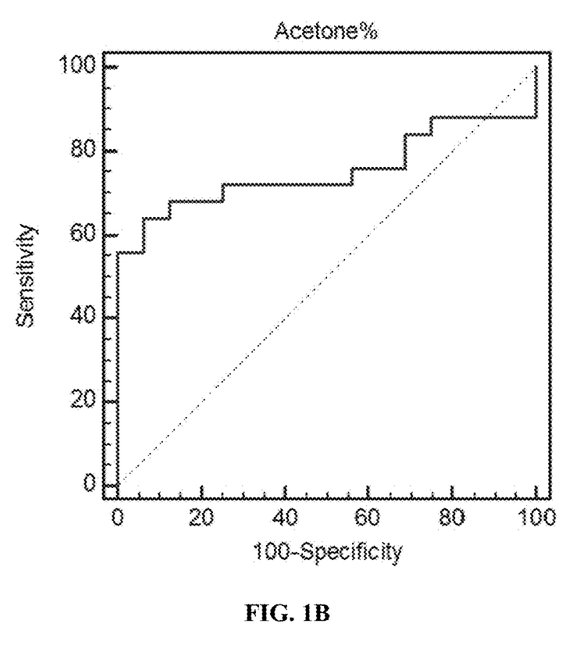
Figure 1C:
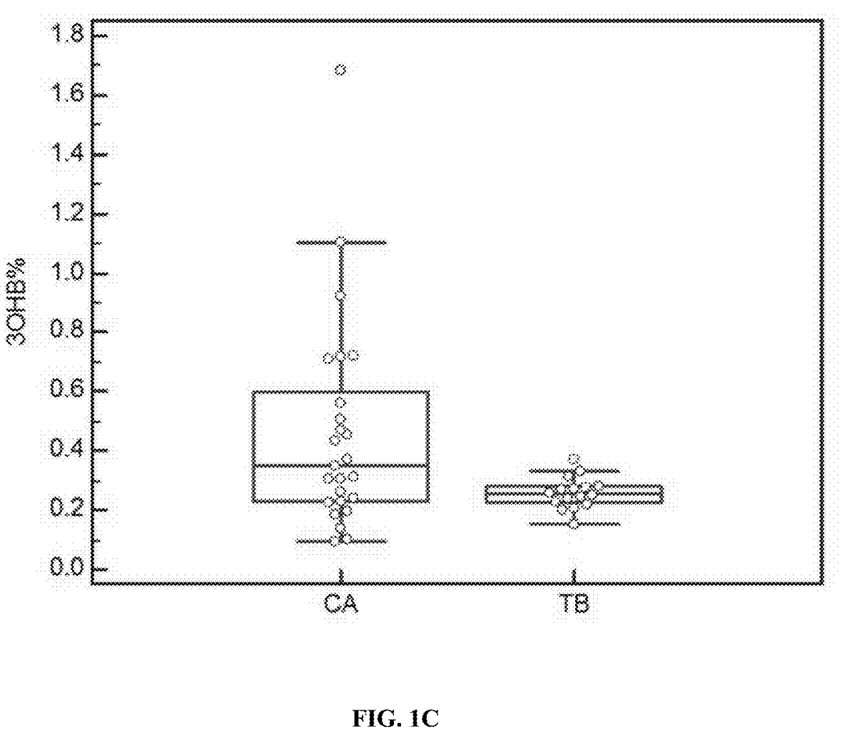
Figure 2:
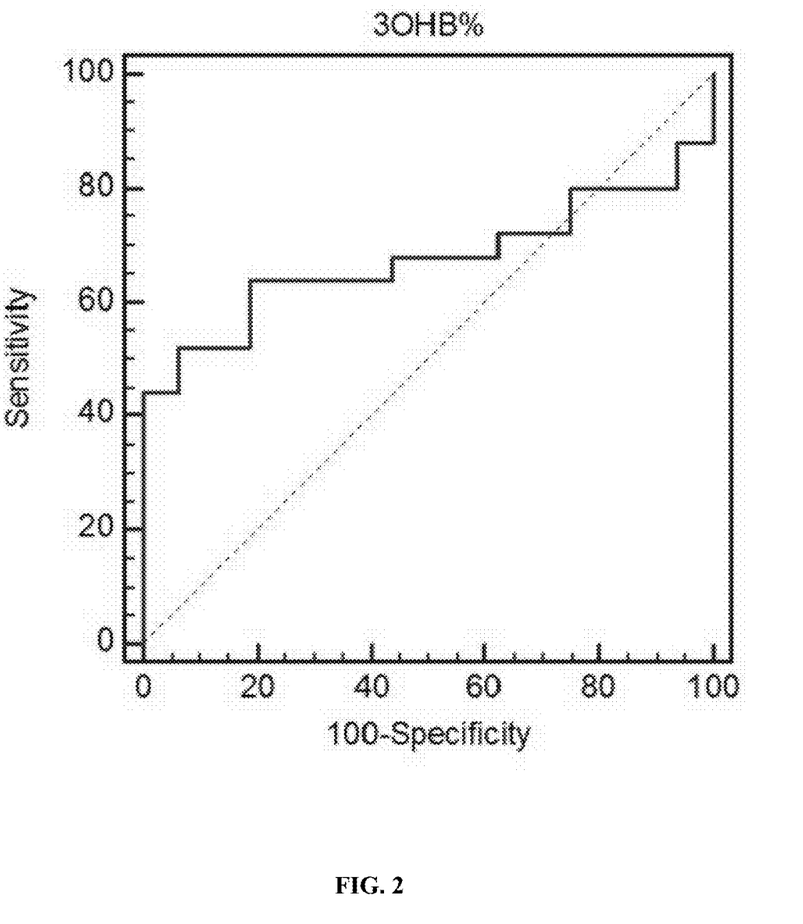

Further, quantification of the PE acetone and 3-hydroxybutyrate using the $^1$H NMR spectra from MPE, tuberculous PE and CHF indicated that these metabolites were significantly elevated in MPE, as shown in FIGS. 1 and 2, and could serve as markers of MPE.

FIG. 1 shows the PE acetone using the 1H NMR spectra from MPE and tuberculous PE (non-MPE) using box plot. The mean acetone level for MPE was 0.25% (95% CI: 0.18-0.31) and the mean acetone level for non-MPE was 0.12% (95% CI: 0.11-0.13). Using Student's t-test, the two groups were significantly different with a p-value of 0.0006 and a fold difference of 2.1×. Using acetone for the diagnosis of MPE, the area-under-ROC was determined to be 0.75 (95% CI: 0.59-0.87) with a sensitivity of 64% (95% CI: 42.5-82.0) and a specificity of 93.8% (95% CI: 69.8-99.8) at the optimal cutoff 0.16% with a p-value of 0.0014.

FIG. 2 shows PE 3-hydroxybutyrate using the 1H NMR spectra from MPE and tuberculous PE (non-MPE) using box plot. The mean 3-hydroxubytyrate level for MPE was 0.46% (95% CI: 0.32-0.61) and the mean 3-hydroxubytyrate level for non-MPE was 0.26% (95% CI: 0.23-0.29). Using Student's t-test, the two groups were significantly different with a p-value of 0.0091 and a fold difference of 1.8×. Using 3-hydroxubutyrate for the diagnosis of MPE, the area-under-ROC was determined to be 0.68 (95% CI: 0.51-0.81) with a sensitivity of 64% (52% CI: 31.3-72.2) and a specificity of 93.8% (95% CI: 69.8-99.8) at the optimal cutoff 0.33% with a p-value of 0.04.

Example 2. NMR-Based Metabolomics Detect Prognostic Biomarkers for MPE

Materials and methods are as described in Example 1.

Important prognostic biomarkers were identified from long survival versus short survival subgroups. Significant prognostic biomarkers were further evaluated using Kaplan-Meier survival analysis with hazard ratio determined.

Using cutoff finder (Budczies et al., *PLoS ONE*, 7(12): e51862. doi:10.1371/journal.pone.0051862(2012)), the optimal cutoff for acetone and 3-hydroxybutyrate were determined to be 0.25% and 0.38%, respectively.

Figure 3:
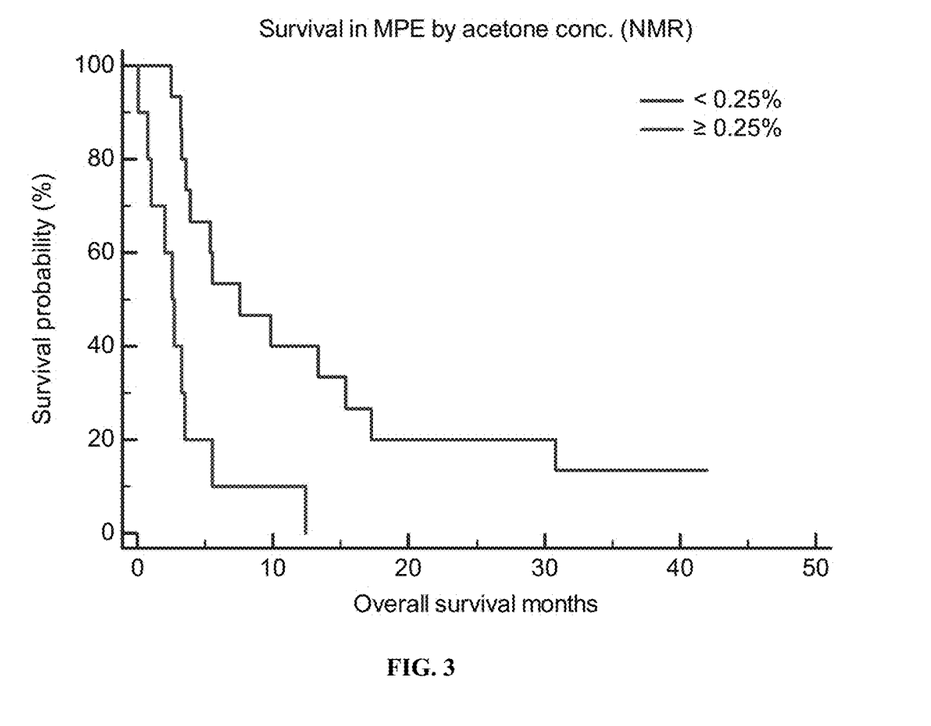
FIG. 3 is a Kaplan-Meier survival curve showing a significantly longer survival time in the low acetone group compared with the high acetone group. The median survival in high acetone and low acetone subgroups were 3.2 months (95% CI: 2.00-3.90) and 13.3 months (5.40-17.2) respectively. The hazard ratio (HR) was determined to be 4.04 (95% CI: 1.6-10.2) with p-value=0.0016.

The prognostic effects of MPE acetone was studied using Kaplan-Meier survival curve and cutoff finder (FIG. 3). The optimal cutoff for acetone was determined to be 0.25%. The hazard ratio (HR) was determined to be 4.04 (95% CI: 1.6-10.2) with p-value=0.0016. The MPE patients were classified according to the cutoff determined into high acetone vs low acetone cancerous PE. There are 13 patients categorized under the high acetone subgroup and 12 patient categorized under the low acetone subgroup. The median survival in high acetone and low acetone subgroups were 3.2 months (95% CI: 2.00-3.90) and 13.3 months (5.40-17.2) respectively.

Figure 4:
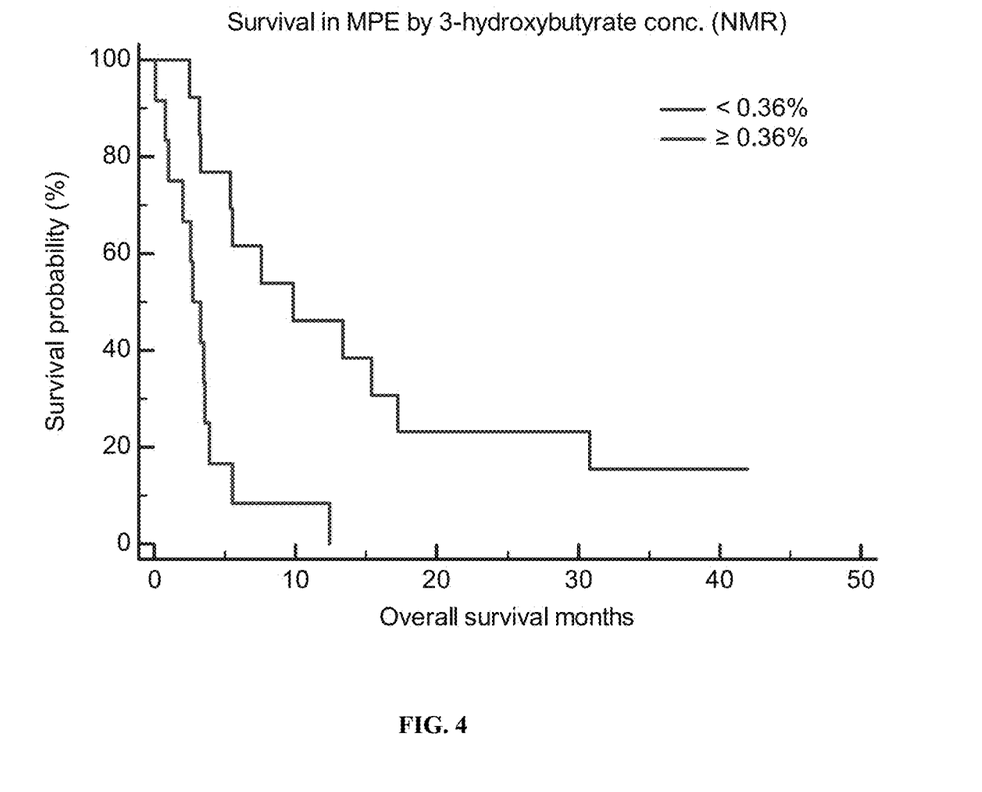
FIG. 4 is a Kaplan-Meier survival curve showing a significantly longer survival time in the low acetone group compared with the high acetone group. The median survival of high 3-hydroxybutyrate and low 3-hydroxybutyrate subgroups were 3.3 months (95% CI=1.00-3.60) and 9.8 months (95% CI=3.90-15.4) respectively. The hazard ratio (HR) was determined to be 4.56 (95% CI: 1.71-12.1) with p-value=0.0011.

For 3-hydroxybutyrate, the optimal prognostic cutoff was determined to be 0.38%. The result of the Kaplan-Meier survival curve was shown in FIG. 4. The hazard ratio (HR) was determined to be 4.56 (95% CI: 1.71-12.1) with p-value=0.0011. The MPE patients were classified according to the cutoff determined into high 3-hydroxybutyrate vs low 3-hydroxybutyrate cancerous PE. There were 10 cases of MPE classified as high 3-hydroxybutyrate subgroup and 15 cases of MPE classified as low 3-hydroxybutyrate subgroup. The median survival of high 3-hydroxybutyrate and low 3-hydroxybutyrate subgroups were 3.3 months (95% CI=1.00-3.60) and 9.8 months (95% CI=3.90-15.4) respectively.

Modifications and variations of the method and kits will be obvious to those skilled in the art from the foregoing detailed description. Such modifications and variations are intended to come within the scope of the appended claims.

I claim:

1. A method of diagnosing a malignant disease or survival term thereof, comprising
    obtaining samples of effusions from a subject in need of diagnosis,
    measuring the normalized intensity of a biomarker selected from the group consisting of acetone, 3-hydroxybutyrate, 1-methylhistamine, 1-methylnicotinamide, 2-methylglutarate, 2-oxoglutarate, 3-OH-3-methylglutarate, 3-methyladipate, 4-aminohippurate, acetone, adenine, alanine, creatine, dimethylamine, formate, fumarate, glucose, glycolate, imidazole, lactate, methylamine, O-acetylcarnitine, oxalacetate, phenylacetylglycine, phenylalanine, tryptophan, tyrosine, cis-aconitate, myo-inositol, trans-aconitate, leucine, valine, acetate, acetoacetate, creatinine, and trimethylalanine-N-oxide in the effusions, and
    comparing the normalized intensity of the biomarker in the effusions of the subject in need of diagnosis and the normalized intensity in a normal or non-diseased subject,
    wherein the subject is diagnosed with a malignant disease when the normalized intensity of the biomarker in the effusion of the subject in need of diagnosis is at least 1.5 fold greater than the normalized intensity of the biomarker in the effusion of the normal or non-diseased subject.

2. The method of claim 1, wherein the normalized intensity of the biomarker in the effusion of the subject in need of diagnosis is not greater than fifty fold the normalized intensity of the biomarker in the effusion of the normal or non-diseased subject.

3. The method of claim 1, wherein the effusion is a pleural effusion, pericardial effusion, peritoneal effusion, subdural effusion, or knee effusion.

4. The method of claim 1, wherein the effusion is pleural effusion.

5. The method of claim 1, wherein measuring the normalized intensity of a biomarker in the effusions is measured with nuclear magnetic resonance (NMR) spectroscopy.

6. The method of claim 5, wherein the NMR spectroscopy is proton NMR spectroscopy.

7. The method of claim 1, wherein the biomarker is acetone.

8. The method of claim 1, wherein the biomarker is 3-hydroxybutyrate.

9. The method of claim 1, wherein the normalized intensities of both acetone and 3-hydroxybutyrate are measured.

10. The method of claim 1, wherein the normalized intensity of acetone in the effusion of the normal or non-diseased subject is 0.12%.

11. The method of claim 1, wherein the normalized intensity of 3-hydroxybutyrate in the effusion of the normal or non-diseased subject is 0.26%.

12. The method of claim 1, wherein the subject is determined to have a malignant disease based on the measured normalized intensity of the biomarker.

13. The method of claim 1, wherein the disease prognosis of the subject is determined based on the measured normalized intensity of the biomarker.

14. The method of claim 1, wherein the biomarker is acetone and the median survival value is less than six months when the normalized intensity of acetone is greater than 0.25%.

15. The method of claim 1, wherein the biomarker is acetone and the median survival value ranges from about six months to about 30 months when the normalized intensity of acetone is less than 0.25%.

16. The method of claim 1, wherein the biomarker is 3-hydroxybutyrate and the median survival value is less than six months when the normalized intensity of 3-hydroxybutyrate is greater than 0.38%.

17. The method of claim 16, wherein the biomarker is 3-hydroxybutyrate and the median survival value ranges from about six months to about 30 months when the normalized intensity of 3-hydroxybutyrate is less than 0.38%.

* * * * *